United States Patent
Bonelli

(10) Patent No.: US 12,257,131 B2
(45) Date of Patent: Mar. 25, 2025

(54) METHOD FOR PRODUCING AN ELASTIC COMPOSITE WEB AND ELASTIC COMPOSITE WEB

(71) Applicant: Fameccanica.Data S.p.A., San Giovanni Teatino (IT)

(72) Inventor: Guido Bonelli, Pescara (IT)

(73) Assignee: Fameccanica.Data S.p.A., San Giovanni Teatino Chieti (IT)

(*) Notice: Subject to any disclaimer, the term of this patent is extended or adjusted under 35 U.S.C. 154(b) by 403 days.

(21) Appl. No.: 17/611,242

(22) PCT Filed: May 12, 2020

(86) PCT No.: PCT/IB2020/054462
§ 371 (c)(1),
(2) Date: Nov. 15, 2021

(87) PCT Pub. No.: WO2020/230012
PCT Pub. Date: Nov. 19, 2020

(65) Prior Publication Data
US 2022/0211548 A1 Jul. 7, 2022

(30) Foreign Application Priority Data
May 16, 2019 (IT) .................. 102019000006819

(51) Int. Cl.
*A61F 13/15* (2006.01)
*A61F 13/49* (2006.01)
(Continued)

(52) U.S. Cl.
CPC .. *A61F 13/15593* (2013.01); *A61F 13/15699* (2013.01); *A61F 13/4902* (2013.01); *B32B 3/266* (2013.01); *B32B 3/28* (2013.01); *B32B 5/04* (2013.01); *B32B 7/12* (2013.01); *B32B 37/144* (2013.01); *B32B 38/1875* (2013.01);
(Continued)

(58) Field of Classification Search
CPC .......... A61F 13/15593; A61F 13/15699; A61F 13/4902; B32B 3/266; B32B 3/28; B32B 5/04; B32B 7/12; B32B 37/144; B32B 38/1875; B32B 2250/03; B32B 2250/40; B32B 2250/02
See application file for complete search history.

(56) References Cited

U.S. PATENT DOCUMENTS

| | | | | |
|---|---|---|---|---|
| 4,397,704 A | * | 8/1983 | Frick | A61F 13/15593 156/472 |
| 2006/0094319 A1 | * | 5/2006 | Schneider | B32B 37/144 442/329 |

FOREIGN PATENT DOCUMENTS

| | | |
|---|---|---|
| EP | 0182942 A1 | 6/1986 |
| EP | 0217032 A2 | 4/1987 |

(Continued)

OTHER PUBLICATIONS

International Search Report and Written Opinion dated Sep. 3, 2020. 11 pages.

*Primary Examiner* — Daniel McNally
(74) *Attorney, Agent, or Firm* — RMCK Law Group PLC

(57) ABSTRACT

A method for producing an elastic composite web for an absorbent sanitary article comprising a first corrugated web and a second web connected together, and at least one elastic element entrapped between said first web and said second web. The invention also relates to an elastic composite web for an absorbent sanitary article.

20 Claims, 3 Drawing Sheets

Figure 6:
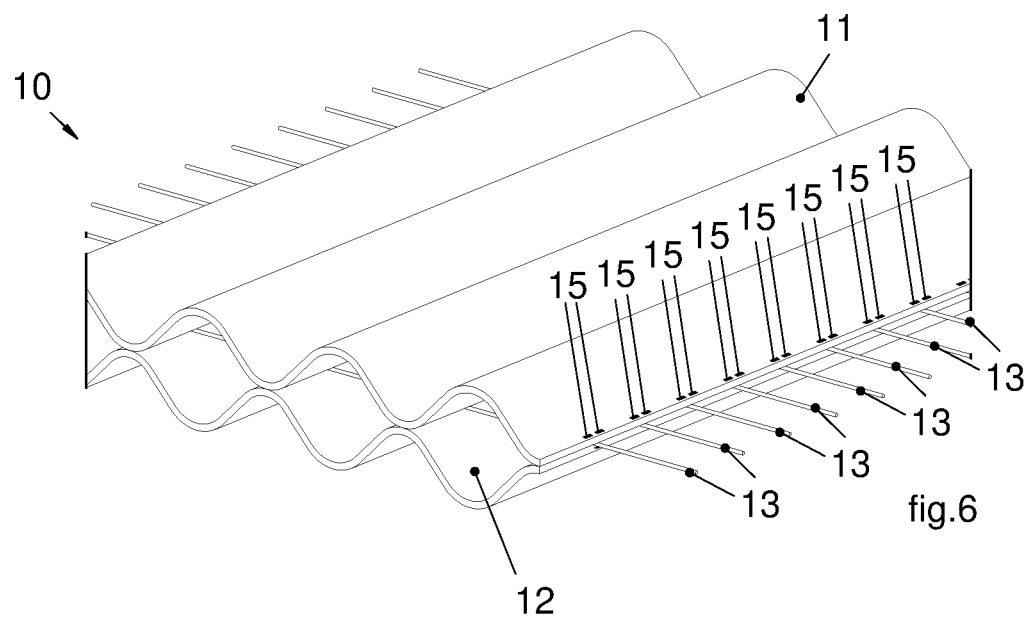

(51) Int. Cl.
  *B32B 3/26* (2006.01)
  *B32B 3/28* (2006.01)
  *B32B 5/04* (2006.01)
  *B32B 7/12* (2006.01)
  *B32B 37/14* (2006.01)
  *B32B 38/00* (2006.01)
(52) U.S. Cl.
  CPC ....... *B32B 2250/03* (2013.01); *B32B 2250/40* (2013.01); *B32B 2555/02* (2013.01)

(56) References Cited

FOREIGN PATENT DOCUMENTS

WO  9534264 A1  12/1995
WO  WO-2017004309 A1 *  1/2017  ....... A61F 13/15585

* cited by examiner

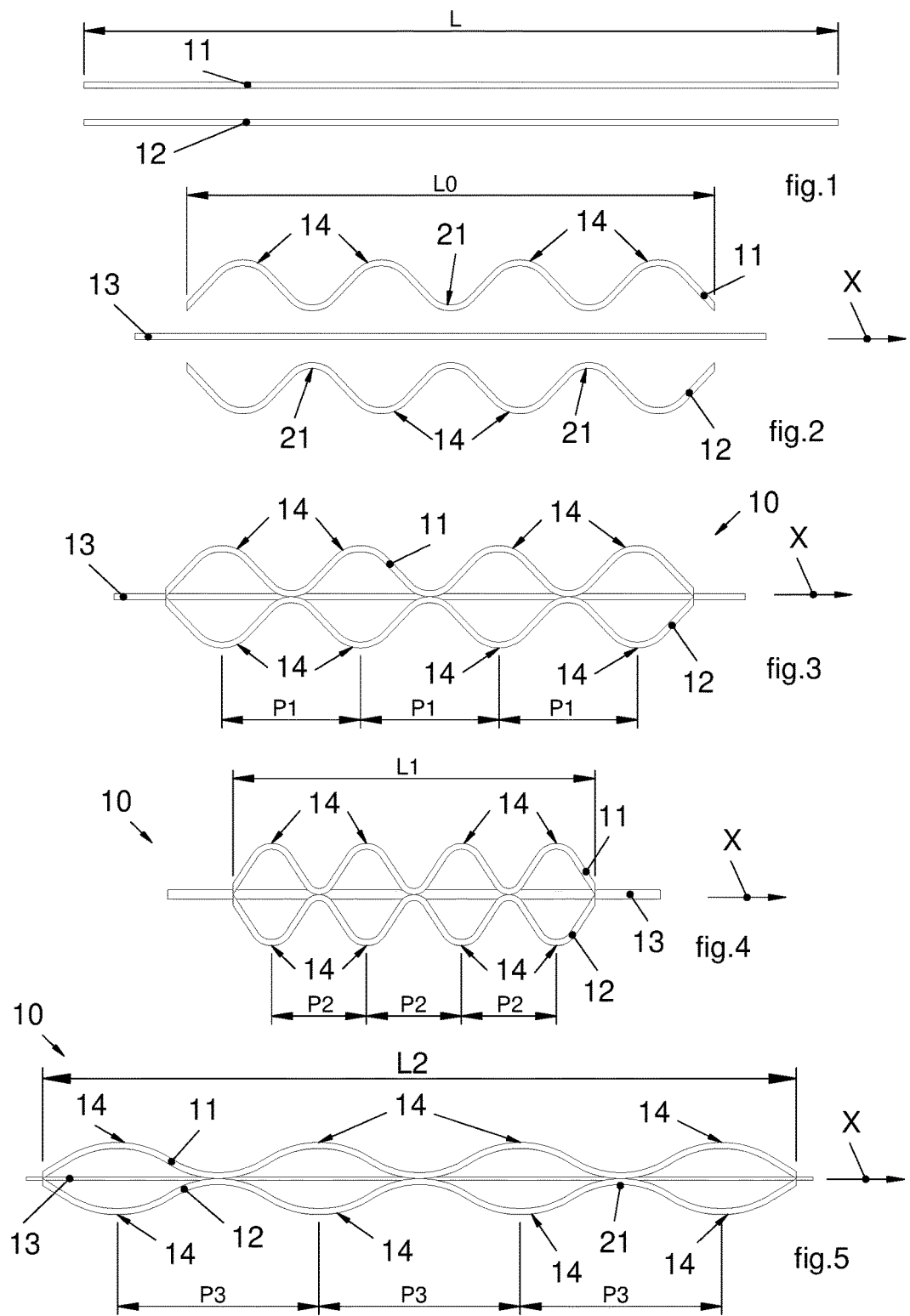

METHOD FOR PRODUCING AN ELASTIC COMPOSITE WEB AND ELASTIC COMPOSITE WEB

CROSS-REFERENCE TO RELATED APPLICATIONS

This application is a 371 National Stage of International Application No. PCT/IB2020/054462, filed May 12, 2020, which claims priority to Italian Patent Application No. 102019000006819 filed May 16, 2019. The disclosure of each of the above applications is incorporated herein by reference in its entirety.

FIELD OF APPLICATION

Embodiments of the present invention relate to a method for producing an elastic composite web.

According to possible embodiments, the elastic composite web can be used in an absorbent sanitary article, such as a diaper, diaper-pants, an incontinence pad, a sanitary towel, or other articles intended to absorb bodily fluids. For example, it can be used to create elastic panels, elastic bands, as well as elastic portions of an absorbent sanitary article.

According to additional embodiments, the elastic composite web can also be used in masks for the mouth and/or nose possibly equipped with a filter used to reduce the possibility of infection and/or diffusion of potentially dangerous contaminants or particles. For example, the elastic composite web can be used to make the elastic bands for wearing a surgical mask, either for the head, or for the ears.

In accordance with possible embodiments, the elastic composite web can also be used in bandages, for covering or containing, applicable in various parts of the body of a subject. For example, these bandages can be used to cover or wrap injured parts of a subject's body. According to possible embodiments, the elastic composite web can also be used to make protective elements or other clothing, such as, for example, shoe covers, disposable socks, caps, or other similar or comparable items.

Embodiments of the present invention relate to an elastic composite web elastically extendable along at least one reference direction.

Embodiments of the present invention also relate to an absorbent sanitary article comprising at least one elastic composite web.

STATE OF THE ART

Absorbent sanitary articles exist made with non-elastic materials which, in relation to the specific absorbent sanitary articles to be made and to the desired wearability to be achieved, can be rendered elastic, for example, by entrapping elastic threads between them.

A typical example of applying elastic threads in a diaper is that of the waist band, or of the containment barriers of the legs, in which pleated regions are made by means of these elastic threads, which provide a certain extensibility to the material.

Known methods entrap pre-tensioned elastic threads between two webs of non-elastic material, such as, for example, a non-woven, locally fixing the webs together and/or the elastic threads tensioned to the webs, so as to locally constrain the elastic threads along an entrapment pattern.

In relation to the specific entrapment pattern and the elastic action that should be obtained for the specific area of the article, the elastic thread is guided along a specific path adjusting the feeding speed and its extension at least during its application on the required component of the absorbent sanitary article.

In the field of absorbent sanitary articles, composite webs comprising coupled webs and between which elastic threads, or other elastic elements are entrapped, are also knowns as elastic composite webs.

These elastic composite webs can be characterized by identifying the relationship between the elongation, or rather between the "strain", and the traction force to which they are subjected, or the "stress".

These relationships are obtained by elongating the elastic composite web along a reference direction by means of an external force, and are typically called Stress-Strain curves in the sector, or S-S curves.

For example, the document EP-A-0803602 illustrates various S-S curves of known elastic composite webs from which it is possible to recognize a breaking zone, wherein at least one of the two webs of the elastic composite web breaks due to the external force to which it is subjected. It is known that one or both of the webs that make up the elastic composite web deform permanently before breaking.

It is known that these elastic composite webs are typically used in the operating area in which they are substantially elastic, that is, in an area where the external force applied is not sufficient to reach the breaking zone.

Typically, the maximum external operating force for which the elastic composite web is intended to be in the operating area, and therefore is substantially elastic, does not exceed 6 N/50 mm.

When the elastic composite web is subject to external forces close to the maximum operating external force, it permanently deforms and the elastic composite web does not return exactly to the same initial rest configuration it had before being subjected to the external force.

The closer the external force is to the maximum operating external force, the greater the deformation, even if up to this force value, it is still possible to consider the behavior of the elastic composite web as being substantially elastic.

Once the maximum operating external force has been exceeded, the effect is significantly pronounced, such that the deformations of one or both of the webs that entrap the elastic bands are very pronounced and uneven.

In the operating area where the elastic composite webs can be considered substantially elastic, they can have elongations ranging from 150% to 250%.

The known elastic composite webs have an extensibility ratio that is not greater than about 3.5 between the length in the extended configuration along a reference direction and the length in the resting configuration along the same reference direction in the operating area.

In other words, by extending one of the known elastic composite webs by means of an external force of not more than 6 N/50 mm along a reference direction, the elastic composite web does not extend, remaining substantially elastic, more than about 3.5 times its resting length along the reference direction.

For example, documents WO-A-2018/189780, WO-A-2018/189781, WO-A-2014/010340, WO-A-2015/137128, and EP-A-3127517 describe known elastic composite webs that have an extensibility ratio between 2 and 3.5.

This aspect represents a severe limitation for absorbent sanitary articles available on the market today, since they have elastic composite webs having limited extensibility in the operating area in which they are substantially elastic.

The possibility of producing absorbent sanitary articles having elastic areas by using elastic composite webs with high elastic capacities plays a first order role, both when considering the structural integrity that is intended to be achieved, for example, in the case of absorbent sanitary articles for incontinence, and in relation to the possibility of producing particular articles with functionally diversified elastic areas.

Depending on the required elasticity, suitably tensioned elastic threads are used which, precisely in relation to the tension to which they are subjected, cannot present a thread count below a threshold value. It is known that this threshold value is about 50 tex, or rather 50 g/km of linear density intended as the thread count of the elastic thread.

In this context, this limit does not allow the use of elastic threads with thin diameters or, in any case, below the threshold value, since it is easy for them to break both during the production step and during use.

However, it is known in the field that, in order to reduce costs and to obtain new types of articles, it is important to provide alternative solutions that allow elastic composite webs to be made with elastic threads having thread counts lower than the current threshold value.

Another problem of the prior art is that known elastic composite webs can present uneven, irregular pleats that are aesthetically unsuitable for the needs of the sector.

During entrapment of the elastic elements between the two webs, or after their entrapment, it is known that it is neither possible to check the uniformity of the resulting pleats, nor to diversify the pleated areas of the elastic composite web in a desired way, both in terms of type and extension.

There are solutions to make an elastic composite web that envisage deforming the two webs before entrapping the elastic threads therein, in particular, these solutions envisage corrugating the webs by stretching them along a direction continuously, or intermittently, so as to obtain corrugated webs having stretched areas.

For example, the document WO-A-2017/004309 describes a method for producing an elastic composite web in which the two webs, before being joined, are subjected to a SELFing operation, or to an incremental stretching.

These operations significantly deform the fibers of the webs and break their bonds because a localized stretching action is exerted, either obtained by means of stretching members intermittently meshed, as in the case of SELFing, or by means of stretching members continuously meshed as in the case of incremental stretching.

In this context, it is not uncommon for the webs that make up the elastic composite web, or even the resulting elastic composite web, to tear during the subsequent processing steps, or during use.

The deformed webs may have a corrugated profile wherein there are stretched areas between one ridge and another. However, these stretched areas can cause localized breakage and/or lacerations of the web which prevent their effective use.

It is also known that a web having ridges alternating with stretched areas has poor tactile qualities, which significantly affect its ergonomics, since the structural discontinuity given by the stretched areas makes the surface of the web rough to the touch and significantly limits its flexibility.

There are solutions that envisage the possibility of corrugating the webs before extruded threads are entrapped therein.

For example, document WO-A-95/34264 describes a method for making a composite web that envisages corrugating the two webs and coupling them to extruded threads.

After being fixed to the two webs, these extruded threads are solidified by cold air so that they take on elastic properties. In this case, the resulting elastic composite web is similar to other elastic composite webs of the prior art, which envisage coupling the webs with resting elastic threads and which, like the elastic threads, shares the limitations set out above.

To summarize what is known from the art of the sector, we can group the known solutions for producing an elastic composite web having pleats into three categories: the first category involves joining the two webs to elastic threads, while the threads are under tension, the second category envisages deforming the webs by stretching them and then coupling them with elastic threads under tension, while the third category envisages corrugating the webs and coupling them to extruded threads which, after being entrapped between the webs, are solidified and made elastic.

There is therefore a need to improve and make a method available for producing an elastic composite web for an absorbent sanitary article, an elastic composite web, as well as an absorbent sanitary article comprising at least one elastic composite web, which overcome at least one of the drawbacks of the prior art.

One object of the present invention is to provide a method for producing an elastic composite web having high extensibility in the operating area, i.e. greater extensibility than those relating to current elastic composite webs with the same applied external force.

Another object of the present invention to provide an elastic composite web capable of being stretched along a reference direction to a greater extent than known elastic composite webs when subjected to external forces less than the maximum operating external force.

Another object of the present invention is to provide an elastic composite web that may comprise elastic threads having thread counts even below the current threshold values, maintaining an even greater extensibility ratio with respect to the current extensibility ratios.

Another object of the present invention is to provide a method that allows a composite elastic web with the desired elastic properties to be produced quickly and simply and which can adapt to the specific manufacturing requirements—periodically required—to obtain absorbent sanitary articles having high extensibility in the desired operating area.

Another object of the present invention is to provide a method that allows provision of an elastic composite web without the fibers of the webs that compose the elastic composite web being stretched and/or weakened, so that the webs are effectively usable and do not present structural discontinuities.

Another object of the present invention is to provide an elastic composite web having better elastic characteristics than the known ones belonging to one of the above categories, and which is obtained by means of a different and original method with respect to those of the prior art.

The present Applicant has devised, tested and implemented this invention to overcome the drawbacks of the prior art, and to obtain these and additional objects and advantages.

SUMMARY OF THE INVENTION

The present invention is expressed and characterized in the independent claims, while the dependent claims set out other characteristics of the present invention or variants of the idea of the main solution.

In accordance with the aforesaid objects, possible embodiments of the present invention relate to a method for producing an elastic composite web comprising a first corrugated web and a second corrugated web provided with ridges alternating with depressions, and connected to each other at these depressions, and at least one elastic element entrapped between the first corrugated web and the second corrugated web.

According to possible embodiments, the elastic composite web can be used to make an absorbent sanitary article.

According to possible embodiments, the elastic composite web can be used to make an air filtering mask.

According to the present invention, the method comprises a corrugation step of the first web and of the second web by means of respective corrugating devices each provided with at least one corrugation surface configured to form the ridges alternating with the depressions along a reference direction, so as to obtain the first corrugated web and second corrugated web.

According to the present invention, the method comprises an entrapment step of the elastic element between the first corrugated web and the second corrugated web, connecting the first corrugated web and the second corrugated web at the depressions.

According to an aspect of the present invention, the corrugation step is carried out before the entrapment step and envisages feeding the first web and the second web towards the respective corrugating devices with a feeding speed greater than the respective movement speed of the corrugating surface.

This aspect is advantageous with respect to the prior art in that the webs are not stretched during corrugation.

By feeding the webs with a speed greater than the movement speed of the corrugation surface, the webs are accumulated inside the respective corrugating device and are arranged gradually and without stretching on the corrugation surface.

In this way, the resulting corrugated webs do not have stretched areas between the ridges and depressions, which occurs in the SELFing or incremental stretching processes where the speed of the stretching and corrugation surface is greater than or at the same limit as that of advancing of the web in order to impart the stretching action on the fibers.

According to an aspect of the present invention, the entrapment step involves entrapping the elastic element while it is under tension along the reference direction.

This aspect allows obtaining elastic composite webs having a greater extensibility than those of the prior art, since the combination of corrugation with the entrapment of elastic threads under tension is advantageously synergistic with respect to the case of the prior art where the extruded threads are coupled to the corrugated webs not under tension before being solidified and made elastic.

Thanks to the combination of the first web and the second web arranged corrugated without stretching with the at least one elastic element under tension, it is possible to obtain an elastic composite web capable of assuming a rest configuration having an extension along the reference direction less than that of the first corrugated web and of the second corrugated web before being connected to each other and wherein the at least one elastic element is entrapped.

The first corrugated web and the second corrugated web are more contracted in the rest configuration than their corrugated extension before being coupled to each other and to the elastic element.

This allows values of the extensibility ratio to be reached that are considerably higher than those known, in the operating area of the elastic composite web in which the web behaves in a substantially elastic way.

In the present disclosure, the extensibility ratio is defined by the ratio between the length of the elastic composite web along the reference direction in an extended configuration, and the length of the elastic composite web at rest along the reference direction.

The values of the extensibility ratio achievable thanks to the present invention allow entrapment of elastic elements under tension by applying even lower tensions than those typically used in the prior art.

With the same value of the required extensibility ratio, the elastic elements can be subjected to lower tensions, since the already corrugated webs contribute to creating a more contracted rest configuration than the known ones.

This aspect makes it possible to quickly and accurately create elastic composite webs with greater extensibility ratios than current ones, and with regular and controlled pleating.

Furthermore, the elastic composite web resulting in the rest configuration has an average number of ridges per centimeter along the reference direction between 10 ridges/cm and 15 ridges/cm.

This number presents a negligible (if not zero) variability and this results in a homogeneous and uniform pleating which allows identification of aligned and defined folds as opposed to the known pleats, which are very random and uneven.

According to possible embodiments, the average number of ridges per centimeter can be detected by measuring the number of ridges per linear centimeter along the reference direction in different areas of the elastic composite web, a plurality of times, and then an average of the measurements carried out is calculated. It is understood that an expert in the field can also use other methods to detect the average number of ridges per centimeter without thereby departing from the scope of the invention.

The resulting elastic composite web has an average distance between the ridges of the first web and the ridges of the second web in the rest configuration between 1.5 mm and 4 mm.

According to possible embodiments, the average distance between the ridges of the first web and the ridges of the second web can be detected by measuring the distance between the ridges of the two webs from a section of the elastic composite web, and then an average of the measurements carried out is calculated. It is understood that an expert in the field can also use other methods to detect the average distance between the ridges of the first web and the ridges of the second web, which can include mechanical measurements of the average thickness of the elastic composite web, or other similar or comparable optical measurements without thereby departing from the scope of the invention.

This aspect allows significant improvement of the tactile sensation as there are no uneven portions or portions folded on themselves, which would make the surface of the elastic composite web wrinkled.

Contrary to the known solutions wherein the uneven pleats can be visible under the clothing, thanks to the combination of the average number of ridges and the average distance between the ridges of the two webs, the elastic composite web according to the present invention has both better functional and structural characteristics than those of the prior art, which translate among the many advantages into better elastic properties, greater tactile softness, and better homogeneity of the pleats.

According to possible embodiments, the method comprises an extrusion step of at least one material and a solidification step of the material to obtain the elastic element, wherein the extrusion step and the solidification step are performed before the entrapment step.

This aspect has the advantage of obtaining an elastic composite web with improved extensibility characteristics with respect to the state of the art and—at the same time—of using elastic elements—obtained by extrusion—that are coupled to the corrugated webs under tension.

In accordance with possible embodiments, the method comprises a perforating step which involves making a plurality of holes at least in the elastic element.

According to possible embodiments, the perforating step involves making a plurality of holes exclusively in the elastic element.

These aspects allow significantly increasing the breathability of the resulting elastic composite web.

According to possible embodiments, the perforating steps involves making a plurality of holes inside the elastic element, so that the side edge of the elastic element is not in contact with the edge of each of these holes. The side edges of the elastic element are the edges defined along the reference direction.

This aspect allows the elastic element at the side edge not to be torn, which in the case of ribbon-like elements could easily lead to the breaking of the elastic element both during the construction of the elastic composite web and during use.

In accordance with possible embodiments, the perforating step starts during the entrapment step.

This aspect allows speeding up the forming process of the elastic composite web and to obtain a breathable elastic composite web.

According to possible embodiments, the entrapment step involves connecting the first corrugated web and the second corrugated web by means of connection areas placed at the holes in the elastic element, wherein the holes have a greater surface extension than that of the connection areas.

This aspect allows obtainment of a breathable elastic composite web—at the same time—without affecting its elastic properties. In this case, the resulting elastic composite web is also structurally stable.

In accordance with possible embodiments, the entrapment step involves entrapping a plurality of elastic elements, and connecting the first corrugated web and the second corrugated web by means of connection areas arranged at the sides of the elastic elements.

According to possible embodiments, the entrapment step envisages entrapping a plurality of elastic elements while at least one of the elastic elements is under tension along the reference direction at a tension different from the tension along the reference direction of at least one other of the elastic elements.

This allows diversifying the elasticity of the elastic composite web in distinct areas in relation to specific production needs.

In accordance with possible embodiments, the entrapment step involves entrapping a plurality of elastic elements and connecting the first corrugated web to the second corrugated web by means of pairs of connection areas arranged at the sides of the elastic elements, and spaced apart by a pitch equal to or less than the transversal extension of the respective elastic element at rest.

This aspect allows locking the elastic elements locally by fastening them at the sides without cutting them. This significantly reduces the possible use of glues and/or adhesives in favor of a greater eco-sustainability of the resulting elastic composite web and a lower weight.

According to possible embodiments, the entrapment step involves entrapping a plurality of elastic elements and connecting the first corrugated web to the second corrugated web by means of pairs of connection areas arranged at the sides of the elastic elements and spaced apart by a pitch greater than the transversal extension of the respective elastic element at rest.

The connection areas in this latter case act as guiding and containment elements of the elastic elements that can slide along the reference direction while remaining within a movement path defined by the connection areas in succession along the reference direction.

The combination of pairs of connection areas spaced apart by a pitch greater than the transverse extension of the elastic element at rest with pairs of connection areas spaced apart by a pitch equal to or less than the transverse extension of the elastic element at rest allows obtainment of an elastic composite web having areas with different well-defined elasticities with the elastic elements each confined within a specific movement path along the reference direction.

According to possible embodiments, the entrapment step involves entrapping a plurality of elastic elements spaced apart along a direction transverse to the reference direction by a constant pitch.

This aspect allows maintaining a uniform and homogeneous aspect of the pleats in the elastic composite web.

In accordance with possible embodiments, the entrapment step involves entrapping a plurality of elastic elements, wherein at least two adjacent elastic elements are spaced apart along a direction transverse to the reference direction by a different pitch from the pitch along the transverse direction of at least two other adjacent elastic elements.

Thanks to this aspect, it is possible to diversify the elasticity of the resulting composite web as it is possible to produce an elastic composite web with dense areas of elastic elements, where the elastic elements are spaced transversely by a first pitch, and sparse areas of elastic elements, where they are spaced apart by a second pitch greater than the first pitch.

In accordance with possible embodiments, the elastic element comprises a thread-like element.

This aspect is advantageous in that by using these thread-like elements it is possible to precisely define the direction along which the resulting composite web is intended to extend.

According to possible variants, the thread-like elements can be arranged and entrapped between the two webs along a desired path, also curved, by means of, for example, thread-guiding devices known in the field.

According to possible embodiments, the elastic element comprises a ribbon-like element.

This aspect allows obtainment of an elastic composite web also having a certain extensibility along a transverse direction with respect to the reference direction. For example, the ribbon-like element can also be applied under tension along a transverse direction with respect to the reference direction.

According to possible variants, the elastic composite web may comprise a plurality of parallel elastic ribbon-like elements. These elastic ribbon-like elements can be obtained by sectioning an elastic ribbon-like web and separating the obtained elastic ribbon-like elements from each other.

This allows obtainment of a plurality of elastic ribbon-like elements from a single elastic ribbon-like web, which being unique requires only one unwinder instead of a plurality of unwinders necessary to process a plurality of elastic ribbon-like elements.

In accordance with possible embodiments, the elastic element comprises adhesive material arranged on the outer surface of the elastic element.

According to possible embodiments, the method envisages that adhesive material is applied at the depressions of the first corrugated web and/or the second corrugated web.

Both of these aspects facilitate the entrapment of the elastic elements, which are coupled by applying mechanical pressure to the two corrugated webs during the entrapment step.

For example, the adhesive material can be applied on contact by means of rotary or other types of members, or by non-contact techniques such as spray dispensers, or other types.

According to possible embodiments, the corrugating devices each comprise a pair of rollers configured to rotate in opposite directions around respective parallel rotation axes and between which the first web or the second web passes, wherein at least one of the rollers has a corrugation surface comprising a plurality of protrusions on which the first web or second web in transit is placed to be corrugated, wherein the speed of movement of the corrugation surface corresponds to the peripheral speed of rotation.

According to possible embodiments, the corrugating devices may comprise clamping plates, or other similar or comparable elements having a plurality of protrusions on their surface facing, during use, towards the web, in which said clamping plates are configured to temporarily fasten the passing web with zero relative speeds at least in the feed direction of the web to produce a corrugated web without stretched areas.

In accordance with possible embodiments, the corrugating devices comprise suction holding means configured to retain the first web or the second web in contact with the respective corrugation surface.

Possible embodiments of the present invention also relate to an elastic composite web.

According to possible embodiments, the present invention also relates to an elastic composite web comprising a first corrugated web and a second corrugated web provided with ridges alternating with depressions, and connected to each other at these depressions, and at least one elastic element entrapped between the first corrugated web and the second corrugated web.

In accordance with possible embodiments, the elastic composite web has a rest configuration, wherein the elastic element is at rest and the elastic composite web has a first length along a reference direction.

According to possible embodiments, the elastic composite web is configured to be elastically extended along the reference direction to assume at least one extended configuration, wherein the elastic composite web has a second length along the reference direction.

According to one aspect of the present invention, the average number of ridges per centimeter along the reference direction in the rest configuration is between 10 ridges/cm and 15 ridges/cm.

According to one aspect of the present invention, the average distance between the ridges of the first web and the ridges of the second web in the rest configuration is between 1.5 mm and 4 mm.

According to possible embodiments, the extensibility ratio defined by the relationship between the second length and the first length is between 4 and 10.

This range of the extensibility ratio is characteristic in that it cannot be reached with the known methods and allows obtainment of elastic composite webs that cannot be obtained with the prior art.

In accordance with possible embodiments, the first web and the second web can be arranged with respective ridges spaced apart by a first pitch along a reference direction and can be connected to each other at the depressions, with the elastic element entrapped at a reference tension along the reference direction between the first web and the second web.

The welding performed at the respective depressions of the first web and the second web allows the mechanical conflicts between the two webs during the elongation and/or contraction of the resulting elastic composite web to be significantly contained.

According to possible embodiments, the ridges can be spaced apart by a second pitch that is smaller than the first pitch in the rest configuration, and by a third pitch that is greater than the first pitch in the extended configuration.

According to possible embodiments, in the extended configuration, the first web and/or the second web are intact, and the elastic composite web is extended along the reference direction by means of an external force less than or equal to 6 N/50 mm.

In accordance with possible embodiments, the elastic element may comprise a thread-like element and/or a ribbon-like element.

According to possible embodiments, the elastic element comprises extruded and solidified material.

In accordance with possible embodiments, the elastic element comprises a plurality of holes.

According to possible embodiments, the holes are placed inside the elastic element, so that the edge of each of these holes is not in contact with a side edge of the elastic element.

According to possible embodiments, the first corrugated web and the second corrugated web are connected by means of connection areas placed at the holes in the elastic element, wherein the holes have a greater surface extension than that of the connection areas.

According to possible embodiments, the first web and the second web can be connected—at least in part—directly to each other.

According to possible embodiments, the first web and the second web are connected by connection areas arranged at the sides of the elastic element.

According to possible embodiments, the first web and the second web are connected by connection areas arranged on the elastic element.

According to possible embodiments, a plurality of elastic elements is entrapped between the first web and the second web, wherein the first web and the second web are connected by connection areas arranged at the sides of the elastic elements.

In accordance with possible embodiments, a plurality of elastic elements is entrapped between the first web and the second web, wherein the first web and the second web are connected by means of pairs of connection areas arranged at the sides of the elastic elements, and spaced apart by a pitch equal to or less than the transverse extension of the respective elastic element at rest.

According to possible embodiments, a plurality of elastic elements is entrapped between the first web and the second web, wherein the first web and the second web are connected by means of pairs of connection areas arranged at the sides of the elastic elements, and spaced apart by a pitch greater than the transverse extension of the respective elastic element at rest.

In accordance with possible embodiments, a plurality of elastic elements is spaced apart along a direction transverse to the reference direction by a constant pitch.

In accordance with possible embodiments, a plurality of elastic elements is entrapped between the first web and the second web, wherein at least two adjacent elastic elements are spaced apart along a direction transverse to the reference direction by a different pitch from the pitch along the transverse direction of at least two other adjacent elastic elements.

In accordance with possible embodiments, the elastic element comprises a thread-like element.

According to possible embodiments, the elastic element comprises a ribbon-like element.

In accordance with possible embodiments, the elastic element comprises adhesive material arranged on the outer surface of the elastic element.

Possible embodiments of the present invention also relate to an absorbent sanitary article comprising an elastic composite web according to any of the embodiments.

Possible embodiments of the present invention also relate to an air filtering mask comprising an elastic composite web according to any of the embodiments.

ILLUSTRATION OF THE DRAWINGS

Figure 7:
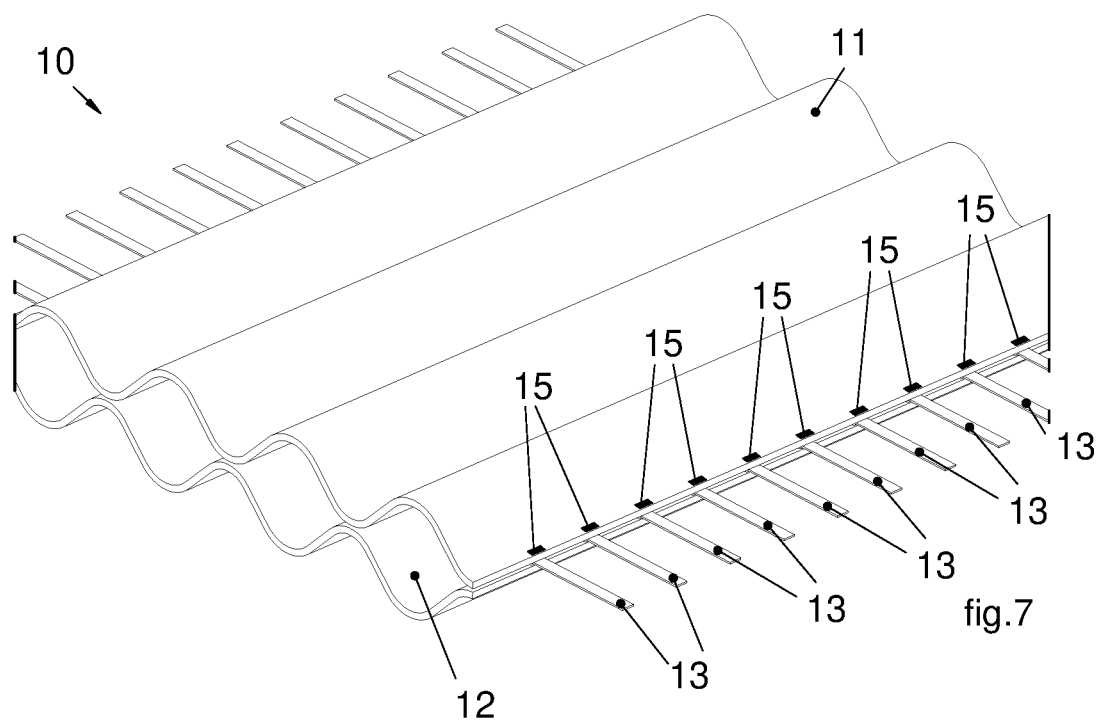
Figure 8:
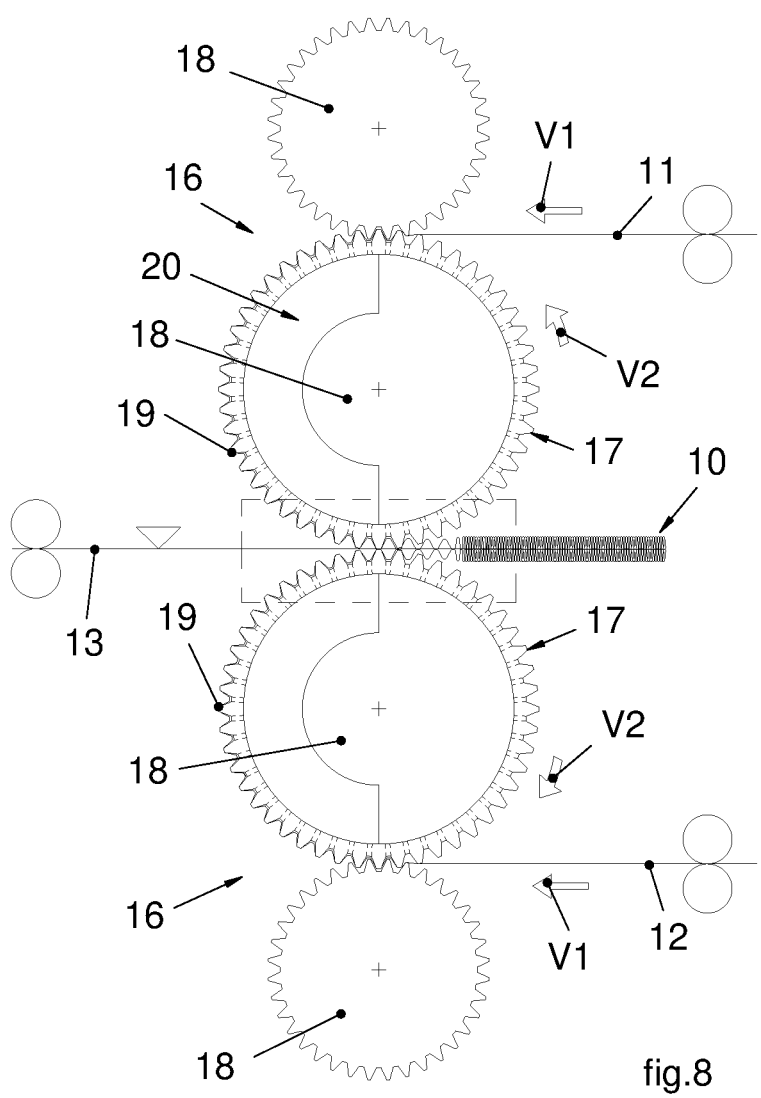
Figure 9:
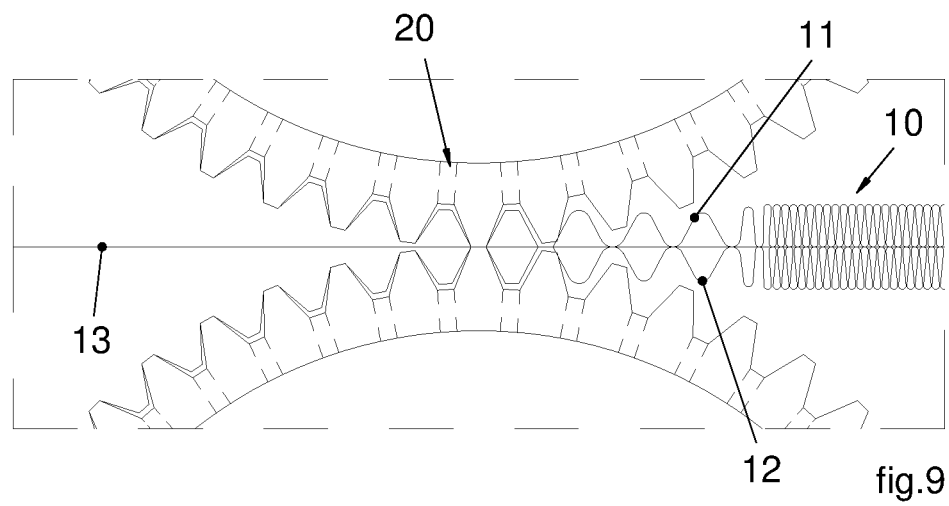

These and other characteristics of the present invention will become clear from the following description of embodiments, given as a non-limiting example, with reference to the attached drawings wherein:

FIGS. 1-5 schematically illustrate an elastic composite web in different construction and operating steps according to possible embodiments of the present invention;

FIGS. 6 and 7 schematically illustrate an elastic composite web according to two possible embodiments of the present invention, FIG. 8 schematically illustrates an exemplary apparatus which carries out the method according to a possible embodiment of the present invention, FIG. 9 illustrates a detail of FIG. 8.

To facilitate understanding, identical reference numbers have been used, where possible, to identify identical common elements in the Figures. It should be understood that elements and characteristics of an embodiment can be conveniently incorporated in other embodiments without further specification.

DESCRIPTION OF THE EMBODIMENTS

Below is a description of some embodiments of the present invention with some variations. This description is an example and not limitative to this, as any further embodiments have also been described with reference to the exposure of the invention.

Embodiments described herein, with reference to the figures, refer to a method for producing an elastic composite web 10, and the related elastic composite web 10.

Although the present invention has an advantageous application in the field of absorbent sanitary articles, reference will be made hereinafter by way of example only, and not limitative to an elastic composite web 10 for an absorbent sanitary article.

For example, an elastic composite web 10 according to the present invention can be used to make the waist band of a diaper, or an incontinence pad.

Further examples of use of the elastic composite web 10 can be identified in the production of elastic panels such as the panels on which mechanical connection means of the hook-loop type, or of another type, are applied.

Other uses may comprise the field of air filtering masks designed to cover the nose and mouth, or containment bands, etc.

According to possible embodiments, the elastic composite web 10 comprises a first corrugated web 11 and a second corrugated web 12, provided with ridges 14 alternating with depressions 21 and connected to each other at the depressions 21, and at least one elastic element 13 entrapped between the first corrugated web 11 and the second corrugated web 12.

According to possible embodiments, the first web 11 and the second web 12 can be connected to each other by means of ultrasonic welding, thermal welding, adhesive materials, glues, their combinations, or by another connection technique.

According to an aspect of the present invention, the method comprises a corrugation step of the first web 11 and of the second web 12 by means of respective corrugating devices 16, each provided with at least one corrugation surface 17 configured to form the ridges 14 alternating with the depressions 21 along a reference direction X, so as to obtain the first corrugated web 11 and the second corrugated web 12.

According to an aspect of the present invention, the method comprises a step for entrapping the elastic element 13 between the first corrugated web 11 and the second corrugated web 12, connecting the first corrugated web 11 and the second corrugated web 12 at the depressions 21.

According to the present invention, the corrugation step is carried out before the entrapment step and envisages feeding the first web 11 and the second web 12 towards the respective corrugating devices 16 with a feeding speed V1 greater than the respective movement speed V2 of the corrugating surface 17.

In accordance with possible embodiments, the feeding speed V1 of the first web 11 and/or of the second web 12 is between 100 meters/minute and 500 meters/minute.

According to possible embodiments, the feeding speed V1 of the first web 11 and/or of the second web 12 is between 150 meters/minute and 350 meters/minute.

In accordance with possible embodiments, the feeding speed V1 of the first web 11 and/or of the second web 12 is substantially equal to 200 meters/minute. In this latter case, an uncertainty is assumed with respect to the value of the feeding speed V1 equal to 10%.

According to possible embodiments, the movement speed V2 is between 50% and 90% of the feeding speed V1.

In accordance with possible embodiments, the movement speed V2 is between 70% and 80% of the feeding speed V1.

According to possible embodiments, the movement speed V2 is substantially equal to 65% of the feeding speed V1. In this latter case, an uncertainty is assumed with respect to the percentage value equal to ±5%.

In accordance with an aspect of the present invention, the entrapment step involves entrapping the elastic element 13 while it is under tension along the reference direction X.

According to possible embodiments, the method envisages:
  arranging the first web 11 and the second web 12 provided with respective ridges 14 alternating with depressions 21, and spaced apart from each other by a first pitch P1 along a reference direction X;

providing at least one elastic element 13;

entrapping the elastic element 13 between the first corrugated web 11 and the second web 12, connecting the first web 11 and the second web 12 together at the depressions 21, while the elastic element 13 is tensioned along the reference direction X to make the elastic composite web 10, wherein the elastic composite web 10 has a rest configuration, wherein the elastic element 13 is at rest and the ridges 14 are spaced apart by a second pitch P2 less than the first pitch P1 along the reference direction X.

In accordance with possible embodiments, the elastic composite web 10 has a rest configuration, wherein the elastic element 13 is at rest and the elastic composite web 10 has a first length L1 along a reference direction X.

According to possible embodiments, the elastic composite web 10 is configured to be elastically extended along the reference direction X to assume at least one extended configuration, wherein the elastic composite web 10 has a second length L2 along the reference direction X.

According to possible embodiments, the average number of ridges 14 per centimeter along the reference direction X is between 10 ridges/cm and 15 ridges/cm.

According to possible embodiments, the average distance between the ridges 14 of the first web 11 and the ridges 14 of the second web 12 in the rest configuration is between 1.5 mm and 4 mm.

According to possible embodiments, the extensibility ratio defined by the relationship between the second length L2 and the first length L1 is between 4 and 10.

This range of the extensibility ratio, as well as the range of the average number of ridges 14 per centimeter, as well as the range of the average distance between the ridges 14 of the two webs 11 and 12, are characteristic in that they cannot be reached by known methods and they allow obtainment of elastic composite webs 10 that cannot be obtained with the prior art.

These characteristic intervals according to the present invention can be obtained thanks to the joint contribution of the pre-corrugation of the first web 11 and the second web 12 with the entrapment of the elastic element 13 under tension. In fact, among the known methods for producing an elastic composite web 10, the method identified according to the present invention is not known.

The value of the extensibility ratio of the elastic composite web 10 is the result of the synergistic effect of the tension imparted to the elastic element 13 at the entrapment moment and of the pre-corrugation of the webs 11 and 12, i.e. the percentage contraction with respect to the extension of webs 11 and 12 laid out before being corrugated.

The synergistic effect is also evident from the possibility of obtaining a high average number of ridges 14 per centimeter, combined with an average distance between the ridges 14 of the two webs 11 and 12 falling within an advantageous range for the uses of the elastic composite web 10.

These parameters allow obtainment of an elastic composite web 10 with a uniform, regular pleating, soft to the touch, without stretched areas, and without ridges 14 folded over the elastic composite web 10, which are typical of the prior art.

With the same value of the extensibility ratio, or other values such as that of the average number of ridges 14 per centimeter or of the average distance between the ridges 14 of the two webs 11 and 12, it is possible to produce an elastic composite web 10 in various ways according to specific needs.

In particular, the elastic composite web 10 can be obtained by tensioning the elastic element 13 to a first tension, and by contracting the first web 11 and the second web 12 by a first contraction percentage value, or by tensioning the elastic element 13 to a second tension greater than the first tension, and by contracting the first web 11 and the second web 12 by a second contraction percentage value that is less than the first contraction percentage value, or by tensioning the elastic element 13 to a third tension, less than the first tension and by contracting the first web 11 and the second web 12 by a third contraction percentage value that is greater than the first contraction percentage.

According to possible embodiments, the extensibility ratio between the second length L2 and the first length L1 can be between 4 and 7.

This additional range of the identified extensibility ratio is even more advantageous in that the effects of hysteresis or other deformations are contained and do not affect the substantially elastic behavior of the elastic composite web 10 in the operating area.

In accordance with possible embodiments, the elastic element 13 may comprise a thread-like element and/or a ribbon-like element, or a plurality of thread-like elements and/or a plurality of ribbon-like elements, or their combinations.

This aspect allows significant containment of the amount of elastic material necessary to make the elastic composite web 10 having the desired elasticity according to the design specifications. In fact, by using more and different thread-like and/or ribbon-like elastic elements 13, or rather, a plurality of elastic threads and/or ribbons, it is possible to obtain elastic composite webs 10 having desired and diversified elasticities.

According to possible embodiments, the entrapment step involves entrapping a plurality of elastic elements 13 spaced apart along a direction transverse to the reference direction X by a constant pitch. In this way, an elastic composite web 10 is obtained in which a plurality of elastic elements 13 are spaced apart along a direction transverse to the reference direction X by a constant pitch.

In accordance with possible embodiments, the entrapment step involves entrapping a plurality of elastic elements 13, wherein at least two adjacent elastic elements 13 are spaced apart along a direction transverse to the reference direction by a different pitch from the pitch along the transverse direction of at least two other adjacent elastic elements. In this way, an elastic composite web 10 is obtained in which at least two adjacent elastic elements 13 are spaced apart along a direction transversal to the reference direction X by a different pitch with respect to the pitch along the transverse direction of at least two other adjacent elastic elements 13.

In the case wherein the elastic elements 13 comprise thread-like elements, or rather elastic threads, by applying lower tensions than those of the prior art to these threads, it is possible to use elastic threads having counts even lower than the current threshold value of the prior art, which is typically about 50 tex.

According to possible embodiments, the thread-like element, or rather, the elastic thread may have a count less than or equal to 50 tex.

According to possible embodiments, the thread-like element, or rather, the elastic thread may have a count from 10 tex to 40 tex.

This allows significant reduction of the production costs, and also simplifies the manipulation of the elastic threads 13 under tension, significantly reducing the possibility that they may break.

Some experimental tests have shown that it is possible to produce an elastic composite web 10 having elastic properties equal to, or even better, than a known elastic composite web having elastic threads with a count of 48 tex.

These experimental tests have shown that, thanks to the present invention, it is possible to produce elastic composite webs 10 having elastic threads with a lower count than the present ones, which have a threshold count of about 50 tex. In particular, the experimental tests carried out have made it possible to create an elastic composite web 10 provided with elastic threads having counts of 31 tex, or 23.5 tex.

For example, it is possible to entrap a plurality of elastic threads 13 between the first web 11 and the second web 12 by arranging them parallel to each other and spaced apart differently.

According to possible embodiments, in the extended configuration, the first web 11 and/or the second web 12 are intact and the elastic composite web 10 is extended along the reference direction X by means of an external force less than or equal to 6 N/50 mm.

This aspect allows the elastic composite web 10 to be used in the operating area in which it has a substantially elastic behavior and without the risk of it breaking.

In accordance with possible embodiments, the first web 11 and the second web 12 can be arranged with respective ridges 14 spaced apart by a first pitch P1 along a reference direction X, and can be connected to each other at the depressions 21, and with the elastic element entrapped at a reference tension along the reference direction X between the first web 11 and the second web 12.

In accordance with possible embodiments, the reference tension can be such as to extend the elastic element 13 with respect to its rest length by a percentage between 150% and 600%.

According to possible embodiments, the entrapment step envisages entrapping a plurality of elastic elements 13 while at least one of the elastic elements 13 is under tension along the reference direction X at a tension different from the tension along the reference direction X of at least one other of the elastic elements 13.

According to possible embodiments, the ridges 14 can be spaced apart by a second pitch P2 smaller than the first pitch P1 in the rest configuration, and a third pitch P3 greater than the first pitch P1 in the extended configuration.

According to possible embodiments, the first web 11 and the second web 12 can be arranged so that they are corrugated, and their contraction along a reference direction X is between 10% and 80% with respect to the length of the respective web 11 and 12 at rest.

In the drawings, the length of the first web 11 and of the second web 12 at rest is indicated by the reference L, while the respective length of the first web 11 and the second web 12, when they are connected together, and to the elastic element 13 at the reference tension, and is indicated by the reference L0.

In accordance with possible embodiments, the first web 11 and the second web 12 can be arranged so that they are corrugated, and their contraction along a reference direction is less than or equal to 50% with respect to the length of the respective web 11 and 12 at rest.

According to possible embodiments, the first web 11 and the second web 12 can be arranged so that they are corrugated, and their contraction along a reference direction X is between 10% and 50% with respect to the length of the respective web 11 and 12 at rest.

According to possible embodiments, the first web 11 and the second web 12 can be arranged so that they are corrugated, and their contraction along a reference direction X is between 20% and 40% with respect to the length of the respective web 11 and 12 at rest.

With respect to the prior art, it is advantageous to pre-corrugate the first web 11 and the second web 12 as this allows obtainment of a precise and controlled corrugation of the resulting elastic composite web 10, avoiding that the composite web has disordered and aesthetically unpleasing pleated areas.

The contraction of the first web 11 and of the second web 12 is carried out before producing the elastic composite web 10 so as to simplify producing the latter, since the level of tensioning of the elastic elements 13 to be entrapped between the first web 11 and the second web 12 is less than that necessary to produce an elastic composite web 10 of the prior art with the same required extensibility.

According to possible embodiments, the corrugation of the first web 11 and/or of the second web 12 can be obtained by means of a respective corrugating device 16.

According to possible embodiments, entrapment of the elastic element 13 can be obtained by means of an entrapment member configured to entrap the elastic element 13 between the first corrugated web 11 and the second corrugated web 12 by connecting the two webs together.

For example, the entrapment member may comprise an anvil pair, welding head cooperating with each other to weld the two webs 11 and 12 together with the elastic element 13 entrapped between the webs.

According to possible embodiments, the entrapment member may comprise one or more passage grooves to pass the elastic element 13 through the entrapment area where the first web 11 and the second web 12 are fixed together.

By way of example, the entrapment member may comprise a pair of rollers with protrusions meshed with each other, wherein at least one roller has welding elements on the respective protrusions which are able to fix the first corrugated web 11 and the second corrugated web 12 together. In this case, the welding elements are positioned so as to define one or more passage grooves for the elastic element 13.

With reference to the drawings, the entrapment member is defined by the corrugating devices 16 which, in addition to performing corrugation, are configured to cooperate in order to entrap the elastic element 13 between the first web 11 and the second web 12. It remains clear that other embodiments that envisage a complete distinction between the corrugating devices 16 and the entrapment member are also included in the present invention.

According to possible embodiments, each of the corrugating devices 16 comprises a pair of rollers 18 configured to rotate in opposite directions around respective parallel rotation axes and between which the first web 11 or the second web 12 passes.

In accordance with possible embodiments, at least one of the rollers 18 has a corrugation surface 17 comprising a plurality of protrusions 19 and on which the first web 11 or the second web 12 is placed in transit to be corrugated.

According to possible embodiments, the movement speed V2 of the corrugation surface 17 corresponds to the peripheral rotation speed of the at least one roller 18 having the corrugation surface 17 itself.

According to possible embodiments, the peripheral rotation speed is between 60 meters/minute and 380 meters/minute.

According to possible embodiments, the peripheral rotation speed is between 120 meters/minute and 150 meters/minute.

In accordance with possible embodiments, each of the corrugating devices 16 comprise suction holding means 20 configured to retain the first web 11 or the second web 12 in contact with the respective corrugation surface 17.

For example, suction openings can be provided on the corrugation surface 17, fluidly connected to a suction source by means of suitable suction channels.

For example, the corrugating device 16 may comprise a pair of rollers 18 provided with a plurality of protrusions 19 suitably meshed and such that during the synchronous movement of the rollers 18, the first web 11 or the second web 12 passing in the space between the two rollers 18 becomes corrugated.

According to possible embodiments, the two rollers 18 are positioned so that the respective protrusions 19 are not in contact. This allows improvement of the performance over time, avoiding unwanted wear and contact.

According to possible embodiments, the protrusions 19 are spaced apart by a pitch between 2 mm and 6 mm, preferably by a pitch between 4.5 mm and 5.5 mm.

According to possible embodiments, the rollers 18 can be provided with welding and/or heated elements suitable for fixing the corrugation. These welding and/or heated elements can be integrated or coupled to the projections 19 of at least one of the two rollers 18.

According to possible embodiments, at least one roller 18 of each corrugating device 16 can be part of the entrapment member.

According to possible embodiments, the first web 11 and/or the second web 12 may comprise a non-woven.

In accordance with possible embodiments, the first web 11 and/or the second web 12 may comprise fibrous materials known in the field of absorbent sanitary articles, such as synthetic fibers, natural fibers, or combinations thereof.

For example, synthetic fibers may comprise polyethylene, polypropylene, polyester, two-component fibers, other synthetic fibers, or combinations thereof. For example, natural fibers may comprise cotton, rayon, viscose, other natural fibers, or combinations thereof.

According to possible embodiments, the first web 11 and/or the second web 12 may comprise a carded non-woven (carded, staple non-woven), and/or a non-woven with a continuous thread (spunbond).

According to possible embodiments, the first web 11 and/or the second web 12 may comprise a Spunbond/Meltblown/Spunbond (SMS) non-woven.

According to possible embodiments, the first web 11 and/or the second web 12 may comprise an Air Through Bond (ATB) non-woven.

According to possible embodiments, the first web 11 and/or the second web 12 may comprise a hydroentangled non-woven.

According to possible embodiments, the first web 11 and/or the second web 12 may comprise a resin-bonded non-woven.

According to possible embodiments, the first web 11 and/or the second web 12 may comprise a needle-punched non-woven.

According to possible embodiments, the first web 11 and/or the second web 12 may comprise a thermobonded non-woven.

According to possible embodiments, the first web 11 and/or the second web 12 may comprise a hydrophobic non-woven.

According to possible embodiments, the first web 11 and/or the second web 12 may comprise a hydrophilic non-woven.

According to possible embodiments, the first web 11 and/or the second web 12 may comprise a non-woven with hydrophobic areas and hydrophilic areas.

According to possible embodiments, the first web 11 and/or the second web 12 may comprise a non-woven having an average grammage between 8 g/m$^2$ and 35 g/m$^2$.

According to possible embodiments, the first web 11 and/or the second web 12 may comprise a non-woven having an average grammage between 10 g/m$^2$ and 20 g/m$^2$.

In accordance with possible embodiments, the method may include a perforating step which involves making a plurality of holes at least in the elastic element 13. Some variants envisage that the resulting elastic composite web 10 also has a plurality of holes in the first corrugated web 11 and/or in the second web 12.

According to possible embodiments, the perforating step involves making a plurality of holes exclusively in the elastic element 13.

In this case, the resulting elastic composite web 10 has the elastic element 13 comprising a plurality of holes.

In accordance with possible embodiments, the perforating step occurs during the entrapment step. For example, it is possible to use the ultrasonic welder to weld the first web 11 and the second web 12 together, while perforating the elastic element 13 by means of the ultrasonic welder itself.

According to possible embodiments, the entrapment step involves connecting the first corrugated web 11 and the second corrugated web 12 by means of connection areas 15 placed at the holes in the elastic element 13, wherein the holes have a greater surface extension than that of the connection areas 15. In other words, the first corrugated web 11 and the second corrugated web 12 are connected through the holes in the elastic element 13.

According to possible embodiments, the first web 11 and/or the second web 12 can be perforated. For example, the first web 11 and/or the second web 12 can be pre-perforated, or they can be perforated in-line with a desired perforated pattern.

According to possible embodiments, the first web 11 and/or the second web 12 may comprise one or more prints.

According to possible embodiments, the first web 11 and/or the second web 12 may comprise a plurality of holes.

According to possible embodiments, both the holes and the prints can be made directly in-line while the elastic composite web 10 is made.

This aspect allows increasing the breathability of the first and/or second web 11, 12 and also, therefore, of the desired area of the absorbent sanitary article comprising this first and second web 11, 12.

According to a possible embodiment, the first web 11 and/or the second web 12 may comprise a thermoplastic polymer in order to facilitate and make the coupling between them (by welding) reliable.

In accordance with possible embodiments, the first web 11 and the second web 12 may have similar or different properties in relation to their orientation during use.

For example, the first web 11 and the second web 12 can be diversified in relation to the degree of softness, the degree of adhesion with the body or with an additional material, the degree of absorption and/or breathability, or in relation to other design characteristics required.

According to possible embodiments, the first web 11 and the second web 12 can be connected—at least in part—directly to each other.

According to possible embodiments, the first web 11 and the second web 12 may be connected by connection areas 15 arranged at the sides of the elastic elements 13.

For example, these connection areas 15 can be made by ultrasonic welding, thermal welding, adhesive elements, glues, or other elements suitable for connecting the first web 11 and the second web 12 together.

In accordance with possible embodiments, a pair of connection areas 15 may comprise a first connection area 15 and a second connection area 15 arranged at the sides of one of the elastic elements 13, and spaced apart by a pitch greater than the transverse extension of the elastic element 13 at rest. For example, if the elastic element 13 comprises an elastic thread, the connection areas 15 are placed at the sides of the elastic thread and spaced apart by a pitch greater than its diameter at rest.

In accordance with possible embodiments, a pair of connection areas 15 may comprise a first connection area 15 and a second connection area 15 arranged at the sides of one of the elastic elements 13 and spaced apart by a pitch equal to or less than the transverse extension of the elastic element 13 at rest. For example, if the elastic element 13 comprises an elastic thread, the connection areas 15 are placed at the sides of the elastic thread and spaced apart by a pitch equal to or less than its diameter at rest.

These embodiments allow entrapment of the elastic elements 13, and in particular the elastic threads, so as to modulate their elasticity with a desired entrapment pattern, which can include portions in which the elastic threads can slide and portions in which they are blocked by a pair of connection areas 15.

According to possible embodiments, the first web 11 and the second web 12 may be connected by connection areas 15 arranged between a pair of elastic elements 13.

This aspect allows additional fixing of the first web 11 to the second web 12 directly, so as to also guarantee the coupling between the first web 11 and the second web 12 between the elastic elements 13, making the elastic composite web 10 stable and with precise pleated areas.

According to possible embodiments, the first web 11 and the second web 12 can be connected at least in part with the elastic element 13 placed between them.

According to possible embodiments, the first web 11 and the second web 12 can be connected by connection areas 15 arranged at the elastic elements 13.

According to possible embodiments, the first web 11 and the second web 12 can be connected by connection areas 15 arranged at the elastic elements 13, wherein each connection area 15 is completely contained within the elastic element 13. This allows the elastic element 13 to be welded without the welding touching the side edges defined along the reference direction X of the elastic element 13. According to possible embodiments, the first web 11 and the second web 12 can be connected through the elastic element 13 by means of connection areas 15.

In accordance with possible embodiments, the elastic element 13 may have holes, through which the first web 11 and the second web 12 can be connected to each other by means of one or more connection areas 15.

According to possible embodiments, the holes in the elastic element 13 can be made while the first web 11 and the second web 12 are connected together.

For example, if the elastic elements 13 comprise ribbon-like elements, it is possible to connect the first web 11 and the second web 12 to each other through the ribbon-like element, creating a connection area 15.

This allows obtainment of a secure anchorage between the first web 11, the second web 12 and the elastic element 13, avoiding—or in any case—significantly containing any mechanical conflicts between the reference direction X along which the elastic elements 13 are applied and the direction transversal to it. These conflict effects are also commonly referred to as mechanical neck-ins.

In accordance with possible embodiments, the first web 11 and/or the second web 12 may comprise an elastic non-woven, or rather, a non-woven capable of extending elastically at least along a reference direction.

According to possible embodiments, the elastic element 13 may comprise materials selected from elastic materials known in the field of the production of disposable absorbent sanitary articles. For example, the elastic element 13 may possibly comprise thermoplastic elastomeric polymers, for example, elastic polyolefins (PE, PP), styrene block copolymers (SIS, SBS, SEBS) possibly mixed with other components, or thermoplastic polyurethanes.

In accordance with possible embodiments, the elastic element 13 may comprise a mixture of elastic polyolefins (PE, PP) and styrene block copolymers (SIS, SBS, SEBS).

According to possible embodiments, the elastic element 13 may comprise elastic glues, or rather elastomers in which plasticizers and tackifiers are present, such as for example resins, or other types of tackifiers.

In accordance with possible embodiments, the elastic element 13 may comprise one or more elastomers whose Melt Flow Index (MFI) value is greater than or equal to 40 g/10 min.

According to possible embodiments, the MFI value can be determined in accordance with defined measurement conditions. By way of non-limiting example, the measurement conditions referring to the indicated values envisage that the temperature is substantially equal to 200° C., and that the load used is 5 kg. For example, the measurement method of the standard MFI ASTM D1238 can be used.

Other conditions for measuring the MFI value can be—at least in part—different from those indicated, but with routine comparison measurements it is possible to determine equivalence.

In accordance with possible embodiments, the elastic element 13 may comprise one or more elastomers whose MFI value is greater than or equal to 100 g/10 min.

In accordance with possible embodiments, the elastic element 13 may comprise one or more elastomers whose MFI value is between 40 g/10 min and 150 g/10 min.

In accordance with possible embodiments, the elastic element 13 may comprise elastic threads, such as, for example, Lycra, Spandex, or other materials.

According to possible embodiments, the elastic element 13 may comprise a monolithic elastic film, or a plurality of ribbon-like elements having desired widths.

In accordance with possible embodiments, the elastic element 13 may comprise an adhesive material arranged on the outer surface of the elastic element 13.

This aspect allows obtainment of a synergistic effect since the adhesive material contributes to the coupling between the first web 11 and the second web 12, containing the use of glue and/or the number of welds necessary to couple the first web 11 and the second web 12 together.

In addition, the adhesive material increases the thickness of the elastic element 13 and consequently its mechanical strength as well.

According to possible embodiments, the method may envisage making the elastic element 13 available by means of extrusion of material which is solidified. This aspect allows various types of elastic elements 13 (in terms of composition and size) to be made available directly in the machine during production of the elastic composite webs 10.

According to possible embodiments, the method comprises an extrusion step of at least one material, and a solidification step of the material to obtain the elastic element 13, wherein the extrusion step and the solidification step are performed before the entrapment step.

In accordance with possible embodiments, the method may involve cooling the extruded material to solidify it, and thus obtaining the elastic element 13 to be entrapped between the first corrugated web 11 and the second corrugated web 12 while being tensioned.

According to possible embodiments, the method may involve adjusting the cross-section of the extruded material during extrusion. For example, this adjustment can be made by adjusting the extrusion section, adjusting the temperature, adjusting the pull of the extruded material, adjusting the extrusion speed, and adjusting combinations of these parameters.

In accordance with possible embodiments, the method may envisage extruding and solidifying a plurality of elastic elements 13 simultaneously.

According to possible embodiments, the elastic elements 13 obtained by extrusion and solidification may have different elastic properties. For example, the elastic elements 13 thus obtained may have different thicknesses, or be cooled at different cooling rates, or undergo other treatments, or be obtained starting from different extruded materials.

According to possible embodiments, the method may envisage extruding one or more elastic elements 13 with a thread count between 10 tex and 50 tex.

Once cooled, the extruded elastic element 13 can be tensioned and entrapped between the first web 11 and the second web 12.

This aspect has the additional advantage that even after entrapment it is possible to condition certain areas of the extruded elastic element 13 by heat treatments and/or mechanical stresses so as to obtain areas where elasticity is at least partially inhibited, preventing the compound that constitutes the elastic element 13 to become stiffened.

It remains clear that conditioning by heat treatments and/or mechanical stresses of some areas of the elastic element 13 can be performed both on elastic elements 13 obtained by extrusion, and on thermoplastic elastic elements 13.

Thanks to the heat and/or mechanical treatment on the extruded elastic element 13, it is possible to return the elastic element to a liquid, or almost liquid phase, so that its elastic properties are inhibited.

According to possible embodiments, the extruded material can be cooled by means of a cooling unit configured to cool the extruded material by means of a cooling source, such as, for example, an air jet at a cooling temperature lower than that of the material.

In accordance with possible embodiments, the extruded material can independently cool by exchanging thermal energy with the environment, or with another passive element, such as, for example, a plate, a roller, or other element of another shape.

According to possible embodiments, the cooling of the extruded material can be carried out by means of coolants, for example, immersion in a cryogenic liquid bath.

In accordance with possible embodiments, the cooling of the extruded material can be carried out by means of a fluid during extrusion, for example nitrogen.

According to possible embodiments, the solidification step occurs simultaneously with the extrusion step of the material. In this way, the extruded material is already solidified at the time of extrusion, for example, by means of nitrogen used at the extruder member, or by means of an extruder member in which a cooling and solidification device is integrated.

A further advantage is that the extruded elastic element 13 may already comprise an adhesive material arranged on the outer surface of the elastic element 13 by means of the extrusion operation.

According to possible embodiments, the adhesive material can be arranged on the outer surface of the elastic element 13 by using a dedicated coating unit configured to deposit the adhesive material on at least part of the outer surface of the elastic element 13.

It is clear that modifications and/or additions of parts can be made to the method for producing an elastic composite web 10 and to the elastic composite web 10 described so far, without thereby departing from the scope of the present invention.

According to possible embodiments, the first web 11 and the second web 12 can be arranged with respective ridges 14 spaced from each other by a first pitch P1 and by a pitch different from the first pitch P1, respectively, along the reference direction X.

According to possible embodiments, the first web 11 can be connected at the depressions 21 to part of the depressions 21 of the second web 12.

According to possible embodiments, part of the depressions 21 of the second web 12 can be connected to the elastic element 13.

Thanks to the possibility of diversifying the pitch of the ridges 14 between the first web 11 and the second web 12, it is possible to create an elastic composite web 10 configured to be elastically extended to assume an extended asymmetrical configuration, in which one web is substantially extended, while the other has ridges 14 spaced apart by a third pitch P3.

In other words, it is possible to obtain an elastic composite web 10 which—in the asymmetrical extended configuration—has one side substantially extended and one pleated side.

This elastic composite web 10 can be worn by a user with the pleated side facing the body so as to have a comfortable surface, and with the substantially extended side facing towards the clothing so as not to perceive the presence of the elastic composite web 10 from the outside.

It is also clear that, although the present invention has been described with reference to some specific examples, a person skilled in the art will certainly be able to produce many other equivalent forms of the method for producing an elastic composite web 10, and of the elastic composite web 10 having the characteristics set forth in the claims, and therefore all falling within the scope of protection defined thereby. In the following claims, the references in brackets have the sole object of facilitating the reading and should not be considered as limiting factors regarding the scope of protection underlying the specific claims.

The invention claimed is:

1. A method for producing an elastic composite web comprising a first corrugated web and a second corrugated web provided with ridges alternating with depressions and connected to each other at said depressions, and at least one elastic element entrapped between said first corrugated web and said second corrugated web, wherein said method comprises:

a corrugation step of said first web and of said second web by means of respective corrugating devices each provided with at least one corrugation surface configured to form said ridges alternating with said depressions along a reference direction, so as to obtain said first corrugated web and said corrugated second web, and an entrapment step of said at least one elastic element between said first corrugated web and said corrugated second web, connecting together said first corrugated web and said second corrugated web at said depressions, wherein the corrugation step is carried out before said entrapment step and involves feeding said first web and said second web towards the respective corrugating devices with a feeding speed greater than respective movement speed of said corrugation surface so as to generate the ridges alternating with said depressions of the first and second corrugated webs without stretching the first and second webs, and wherein said entrapment step involves entrapping said at least one elastic element while it is under tension along said reference direction.

2. The method according to claim 1, comprising an extrusion step of at least one material and a solidification step of said material to obtain said at least one elastic element, wherein said extrusion step and said solidification step are carried out before said entrapment step.

3. The method according to claim 2, wherein said solidification step occurs simultaneously with said extrusion step of said material.

4. The method as in claim 2, wherein said entrapment step involves entrapping a plurality of said elastic elements and connecting said first corrugated web and said second corrugated web by means of pairs of connection areas arranged at sides of said plurality of elastic elements and spaced apart by a pitch greater than a transverse extension of the respective elastic element at rest.

5. The method as in claim 1, wherein said at least one elastic element comprises adhesive material arranged on an outer surface of said at least one elastic element.

6. The method as in claim 5, wherein adhesive material is applied at said depressions of said first corrugated web and/or said second corrugated web.

7. The method as in claim 1, wherein said entrapment step involves entrapping a plurality of said elastic elements and connecting said first corrugated web and said second corrugated web by means of connection areas arranged at sides of said plurality of elastic elements.

8. The method as in claim 1, wherein said entrapment step involves entrapping a plurality of said elastic elements while at least one of said plurality of elastic elements is under tension along said reference direction, at a different tension from the tension along said reference direction of at least one other of said plurality of elastic elements.

9. The method as in claim 1, wherein said entrapment step involves entrapping a plurality of said elastic elements, and connecting said first web and said second web by means of pairs of connection areas arranged at sides of said plurality of elastic elements and spaced apart by a pitch equal to or less than a transverse extension of the respective elastic element at rest.

10. The method as in claim 1, wherein said entrapment step involves entrapping a plurality of said elastic elements spaced apart along a direction transverse to said reference direction by a constant pitch.

11. The method as in claim 1, wherein said entrapment step involves entrapping a plurality of said elastic elements, and wherein at least two of said elastic elements adjacent to each other are spaced apart along a direction transverse to said reference direction by a pitch different with respect to a pitch along said transverse direction of at least two other adjacent elastic elements of the plurality of elastic elements.

12. The method as in claim 1, wherein said at least one elastic element comprises a thread-like element.

13. The method as in claim 1, wherein said at least one elastic element comprises a ribbon-like element.

14. The method as in claim 1, wherein said corrugating devices each comprise a pair of rollers configured to rotate in opposite directions around respective parallel rotation axes, and between which said first web or said second web passes, wherein at least one of said rollers has said corrugation surface comprising a plurality of protrusions on which said first web or said second web is placed in transit to be corrugated, and wherein said movement speed of said corrugation surface corresponds to a peripheral rotation speed.

15. The method as in claim 1, wherein said corrugating devices comprise a suction holding arrangement configured to hold said first web or said second web in contact with the respective corrugation surface.

16. A method for producing an elastic composite web comprising a first corrugated web and a second corrugated web provided with ridges alternating with depressions and connected to each other at said depressions, and at least one elastic element entrapped between said first corrugated web and said second corrugated web, wherein said method comprises:

a corrugation step of said first web and of said second web by means of respective corrugating devices each provided with at least one corrugation surface configured to form said ridges alternating with said depressions along a reference direction, so as to obtain said first corrugated web and said corrugated second web, and an entrapment step of said at least one elastic element between said first corrugated web and said corrugated second web, connecting together said first corrugated web and said second corrugated web at said depressions, a perforating step, which involves making a plurality of holes at least in said at least one elastic element, wherein the corrugation step is carried out before said entrapment step and involves feeding said first web and said second web towards the respective corrugating devices with a feeding speed greater than respective movement speed of said corrugation surface, and wherein said entrapment step involves entrapping said at least one elastic element while it is under tension along said reference direction.

17. The method as in claim 16, wherein said perforating step involves making a plurality of holes exclusively in said at least one elastic element.

18. The method as in claim 16, wherein said perforating step occurs during said entrapment step.

19. The method as in any one of claim 16, wherein said perforating step involves making a plurality of holes within said at least one elastic element, so that a side edge of said at least one elastic element is not in contact with an edge of each of said plurality of holes.

20. The method as in claim 16, wherein said entrapment step involves connecting said first corrugated web and said second corrugated web by means of connection areas placed at said plurality of holes in said elastic element, wherein said plurality of holes have a surface extension greater than that of said connection areas.

\* \* \* \* \*